United States Patent
Aldar (10) Patent No.: US 12,343,122 B2
(45) Date of Patent: *Jul. 1, 2025

(54) ORAL ECG DEVICE

(71) Applicant: OMNYSENSE LTD., Tel-Aviv (IL)

(72) Inventor: Yossi Aldar, Tel-Aviv (IL)

(73) Assignee: OMNYSENSE LTD., Tel-Aviv (IL)

(*) Notice: Subject to any disclaimer, the term of this patent is extended or adjusted under 35 U.S.C. 154(b) by 830 days.

This patent is subject to a terminal disclaimer.

(21) Appl. No.: 17/555,885

(22) Filed: Dec. 20, 2021

(65) Prior Publication Data

US 2022/0110533 A1    Apr. 14, 2022

Related U.S. Application Data

(63) Continuation-in-part of application No. PCT/IL2020/050874, filed on Aug. 11, 2020.
(Continued)

(51) Int. Cl.
 *A61B 5/0205* (2006.01)
 *A61B 5/00* (2006.01)
(Continued)

(52) U.S. Cl.
 CPC .......... *A61B 5/02055* (2013.01); *A61B 5/002* (2013.01); *A61B 5/0533* (2013.01);
(Continued)

(58) Field of Classification Search
 CPC ....... A61B 5/02055; A61B 5/282; A61B 5/26; A61B 5/25; A61B 5/002; A61B 5/0533;
(Continued)

(56) References Cited

U.S. PATENT DOCUMENTS 9,161,697 B2    10/2015   Azimi
2010/0234746 A1  9/2010   Sebelius
(Continued)

FOREIGN PATENT DOCUMENTS

CN    103584871 A    2/2014
CN    205107641 U    3/2016
(Continued)

OTHER PUBLICATIONS

Nelwan, S. P et al. "Correction of ECG variations due to non-standard electrode positions." Computers in Cardiology 2001. Vol. 28 (Cat. No. 01CH37287). IEEE, 2001. Sep. 26, 2001; doi: 10.1109/CIC.2001.977656.

(Continued)

*Primary Examiner* — Linda C Dvorak
*Assistant Examiner* — Abigail Bock
(74) *Attorney, Agent, or Firm* — The Roy Gross Law Firm, LLC; Roy D. Gross (57) ABSTRACT

An oral ECG device in the shape of a digital thermometer for recording an ECG and temperature of an individual comprises: a mouthpiece further comprising a temperature sensor; the mouthpiece insertable into an individual's mouth; a body further comprising a proximal electrode and a distal electrode for recording Lead-I of an ECG, the proximal and distal electrodes are holdable by left and right hands of the individual; each hand being in an electric contact with one of the proximal and distal electrodes; and a microcontroller preprogrammed for processing electric signals from the temperature sensor, proximal electrode and distal electrode. The proximal and distal electrodes are holdable by left and right hands in either orientation and the temperature sensor is positioned within individual's mouth in a contemporaneous manner.

10 Claims, 7 Drawing Sheets

Related U.S. Application Data (60) Provisional application No. 62/863,890, filed on Jun. 20, 2019.

(51) Int. Cl.
*A61B 5/0533* (2021.01)
*A61B 5/08* (2006.01)
*A61B 5/1455* (2006.01)
*A61B 5/25* (2021.01)
*A61B 5/26* (2021.01)
*A61B 5/282* (2021.01)
*G16H 40/67* (2018.01)
*G16H 50/20* (2018.01)
*A61B 5/332* (2021.01)

(52) U.S. Cl.
CPC ........ *A61B 5/0816* (2013.01); *A61B 5/14552* (2013.01); *A61B 5/25* (2021.01); *A61B 5/26* (2021.01); *A61B 5/282* (2021.01); *A61B 5/682* (2013.01); *G16H 40/67* (2018.01); *G16H 50/20* (2018.01); *A61B 5/332* (2021.01); *A61B 2560/045* (2013.01); *A61B 2562/0271* (2013.01)

(58) Field of Classification Search
CPC ... A61B 5/0816; A61B 5/14552; A61B 5/682; A61B 5/332; A61B 2560/045; A61B 2562/0271; G16H 40/67; G16H 50/20
See application file for complete search history.

(56) References Cited

U.S. PATENT DOCUMENTS

| | | |
|---|---|---|
| 2013/0035602 A1 | 2/2013 | Gemer |
| 2013/0253286 A1 | 9/2013 | Fridman |
| 2015/0045629 A1 | 2/2015 | Azimi |
| 2016/0135701 A1 | 5/2016 | Drake |
| 2016/0287128 A1 | 10/2016 | Jain et al. |
| 2018/0098620 A1 | 4/2018 | Lee et al. |
| 2018/0110418 A1 | 4/2018 | Fridman et al. |

FOREIGN PATENT DOCUMENTS

| | | |
|---|---|---|
| CN | 205493819 U | 8/2016 |
| CN | 106999082 A | 8/2017 |
| EP | 2835100 B1 | 2/2015 |
| KR | 102135407 B1 | 7/2020 |

OTHER PUBLICATIONS

Mason et al. "Recommendations for the standardization and interpretation of the electrocardiogram: part II: the electrocardiogram and its technology a scientific statement from the American Heart Association Electrocardiogra and Arrhythmias Committee, Council on Clinical Cardiology; the American College of Cardiology Foundation; and the Heart Rhythm Society endorsed by the International Society for Computerized Electrocardiology." Journal of the American College of Cardiology 49.10 (2007): 1109-1127. Mar. 13, 2007; Doi: 10.1161CIRCULATIONAHA. 106.180201.

PCT International Search Report for International Application No. PCT/IL2020/050874, mailed Nov. 19, 2020, 4pp.

PCT Written Opinion for International Application No. PCT/IL2020/050874, mailed Nov. 19, 2020, 6pp.

Papadatou-Pastou, M et al. (2020). Human handedness: A meta-analysis. PsychologicalBulletin. 146 (6): 481-524 .; Retrieved Dec. 20, 2021 from: https://doi.org/10.1037/bul0000229.

Mody, P et al. (2015). Fever-Induced Electrocardiogramges. J Gen Intern Med. Jan. 2015; 30(1): 136-137. Published online Sep. 1, 20140. doi: 10.1007/s11606-014-2992-9. Pmcid: PMC4284273.

Mody et al. Fever-induced electrocardiogramanges. J Gen Intern Med. Jan. 2015;30(1):136-7. doi: 10.1007/s11606-014-2992-9. Epub Sep. 10, 2014. PMID: 25205622; PMCID: PMC4284273.

Papadatou-Pastou et al. Human handedness: A meta-analysis. Psychol Bull. Jun. 2020; 146(6):481-524. doi: 10.1037/bul0000229. Epub Apr. 2, 2020. PMID: 32237881.

Extended European Search Report for European Patent Applicant No. 20826070.3, dated Jun. 20, 2022, 11pp.

The State Intellectual Property Office of the People's Republic of China, The First Office Action for Chinese Patent Application No. 202080057757.8, dated Oct. 19, 2024, 21pp.

ORAL ECG DEVICE

CROSS-REFERENCE TO RELATED APPLICATIONS

This application is a Continuation-in-part (CIP) Patent Application of PCT Patent application No. PCT/IL2020/050874 having the International filing date of Aug. 11, 2020, which claims the benefit of priority of U.S. Provisional Patent Application No. 62/863,890, filed Jun. 20, 2019, the contents of which are all incorporated herein by reference in their entirety.

FIELD OF THE INVENTION

The present invention relates to electrocardiography and, more particularly, oral ECG devices.

BACKGROUND OF THE INVENTION

Figure 1A:
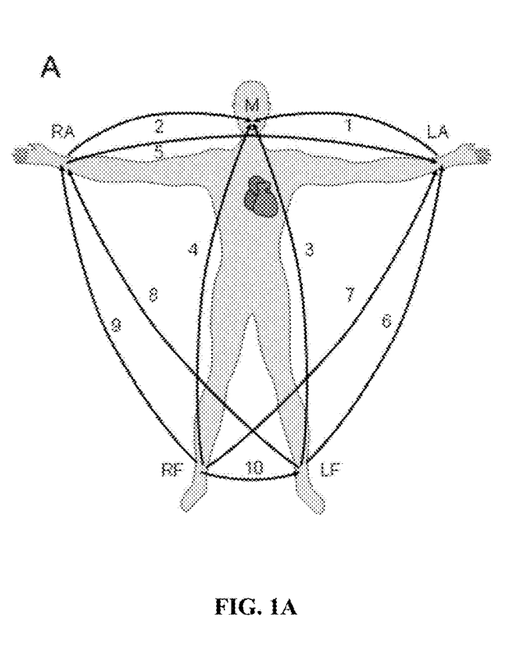
FIGS. 1a and 1b show the Waller scheme for an ECG versus the classic scheme for an ECG, respectively.

The pioneer of electrocardiograms, A. D. Waller, first recorded an electrocardiogram (ECG) in man using surface electrodes in 1887. He invented a scheme involving 5 body locations for electrodes, with 10 leads interconnecting them, as shown in FIG. 1a. In Waller's arrangement, the mouth is one of the body locations, and Lead-1 in Woller's scheme is the lead connecting the mouth (M) to the left-arm (LA). Lead-2 in this scheme connects mouth (M) to right-arm (RA), whereas Lead-5 connects LA to RA. There were numerous practical problems with this scheme; and it has since been supplanted by the ECG connection scheme created by W. Einthoven, who invented the first practical electrocardiograph (ECG or EKG) in 1895 and received the Nobel Prize in Physiology or Medicine for it in 1924.

The practical problems of the Waller scheme include (a) the need to somehow connect an electrode to the mouth, and (b) the poor quality of the ECG signal along Lead-2 as its electrical path through the body largely does not pass near the heart and is therefore not efficient for detecting the heart's electrical activity. The Einthoven scheme resolves these problems (and others) by using three body locations to form a triangle around the heart, where Lead-I connects LA to RA; constituting the classic arrangement for a 1-Lead ECG.

Prior art using the Waller scheme includes US 2018/0110418 (Fridman, G. Y. et al.), which describes a handheld device for one-handed operation in which one electrode is positioned on the thumb on/off button of said device, while the other electrode is positioned on the mouthpiece. Although 90% of people are right-handed ("*Human handedness: A meta-analysis*". Psychological Bulletin. 146 (6): 481-524; Papadatou-Pastou, M; et. al), the user of this device is required to hold it in their left hand in order to implement the Waller Lead-1, which is counter-intuitive. However, if they were to hold it in the more intuitive right hand, then the lead implemented would be Waller Lead 2, which yields a weak signal. In either case, the ECG trace yielded would not be the classic one expected for building an Average Complex, from which standard calculated cardiac parameters can be derived. Additionally, as it is impossible in the embodiment described to enforce the use of a specific hand, the results could well be inconsistent—with a user sometimes using one hand and sometimes the other.

SUMMARY OF THE INVENTION

It is hence one object of the invention to disclose an oral ECG device in the shape of a digital thermometer for measuring an ECG and temperature of an individual. The aforesaid oral ECG device comprises: a mouthpiece further comprising a temperature sensor; said mouthpiece insertable into an individual's mouth; and a body further comprising a proximal electrode and a distal electrode for recording Lead-I of an ECG, said proximal and distal electrodes are holdable by left and right hands of said individual; each hand being in an electric contact with one of said proximal and distal electrodes; a microcontroller preprogrammed for processing electric signals from said temperature sensor, proximal electrode and distal electrode.

The purpose of the present invention is to provide proximal and distal electrodes holdable by left and right hands, while said temperature sensor is positioned within an individual's mouth in a contemporaneous manner.

Another object of the invention is to disclose the device further comprising a sensor selected from the group consisting of a pulse-oximetry sensor and a microphone arranged for in-mouth operation, and the combination thereof.

Another object of the invention is to disclose the device further comprising communication means selected from the group consisting of Bluetooth, WiFi, and 3G/4G/5G and any combination thereof.

Another object of the invention is to disclose a system for viewing the Lead-I ECG trace generated comprising: at least one oral ECG device in the shape of a digital thermometer for recording an ECG signal and temperature of an individual; said oral ECG device comprising: a mouthpiece further comprising a temperature sensor; said mouthpiece insertable into an individual's mouth; and a body further comprising a proximal electrode and a distal electrode for recording Lead-I of an ECG, said proximal and distal electrodes being holdable by left and right hands of said individual; each hand being in an electric contact with one of said proximal and distal electrodes; a microcontroller preprogrammed for processing electric signals from said temperature sensor, proximal electrode and distal electrode; said proximal and distal electrodes are holdable by left and right hands, where said temperature sensor is positioned within individual's mouth in a contemporaneous manner; and a local device or remote server in wired or wireless communication with said device configured for processing and displaying said Lead-I ECG trace.

Another object of the invention is to disclose the system further configured for calculating and/or presenting an Average Complex and/or cardiac parameters derived from said Average Complex.

Another object of the invention is to disclose the local device or remote server preprogrammed for providing said Lead-I ECG trace in an orientation-independent manner by summing data points therealong, determining an orientation of said Lead-I ECG trace and inverting said orientation of said Lead-I ECG as needed Another object of the invention is to disclose the method of measuring an ECG and temperature of an individual. The aforesaid method comprises steps of: providing an oral ECG device in the shape of a digital thermometer for recording the ECG and temperature of an individual; said oral ECG device comprising: a mouthpiece further comprising a temperature sensor; said mouthpiece insertable into an individual's mouth; and a body further comprising a proximal electrode and a distal electrode for recording Lead-I of an ECG, said proximal and distal electrodes are holdable by left and right hands of said individual; each hand being in an electric contact with one of said proximal and distal electrodes; a microcontroller preprogrammed for processing electric signals from said temperature sensor, proximal electrode and distal electrode; said proximal and distal electrodes are holdable by left and right hands when said temperature sensor is positioned within individual's mouth in a contemporaneous manner; holding said proximal and distal electrodes by said left and right hands in a separate manner and inserting said temperature sensor into said mouth in contemporaneous manner; and measuring electric signals from said temperature sensor, proximal electrode and distal electrode.

Another object of the invention is to disclose the method comprising steps of providing a sensor selected from the group consisting of a pulse-oximetry sensor, a microphone arranged for in-mouth operation and combination thereof and measuring electric signals therefrom.

Another object of the invention is to disclose the method according to claim 9 comprising step of communicating with an external device or a server by means of communication means selected from selected from the group consisting of Bluetooth, WiFi, and 3G/4G/5G and any combination thereof.

Another object of the invention is to disclose a method for viewing a Lead-I ECG trace comprising: providing at least one oral ECG device in the shape of a digital thermometer for measuring an ECG signals and temperature of an individual; said oral ECG device comprising: a mouthpiece further comprising a temperature sensor; said mouthpiece insertable into an individual's mouth; and a body further comprising a proximal electrode and a distal electrode for measuring Lead-I, said proximal and distal electrodes are holdable by left and right hands of said individual; each hand being in an electric contact with one of said proximal and distal electrodes; a microcontroller preprogrammed for processing electric signals from said temperature sensor, proximal electrode and distal electrode; said proximal and distal electrodes are holdable by left and right hands and said temperature sensor is positioned within individual's mouth in a contemporaneous manner; a local device or remote server in wire or wireless communication with said device configured for processing and displaying said Lead-I ECG trace; holding said proximal and distal electrodes of said at least one oral ECG device by said left and right hands in a separate manner and inserting said temperature sensor of said at least one oral ECG device into said mouth in contemporaneous manner; and measuring electric signals from said temperature sensor, proximal electrode and distal electrode; transmitting measured electric signals to said local device or remote server; processing said measured electric signals such that said Lead-I ECG trace is obtained; and displaying said Lead-I ECG trace.

Another object of the invention is to disclose the method comprising a step of calculating and/or presenting an Average Complex and/or cardiac parameters derived from said Average Complex.

Another object of the invention is to disclose the method comprising a step of providing said Lead-I ECG trace in an orientation-independent manner by summing data points therealong, determining an orientation of said Lead-I ECG trace and inverting said orientation of said Lead-I ECG as needed It is therefore an object of the invention to provide a hand-held ECG device shaped and implemented like a household oral digital thermometer and including a temperature sensor within its tip, which overcomes the limitations of the prior art;

It is a further object of the invention to have said device enable presentation of the classic Lead-I ECG trace on a local or remote display.

It is a further object of the invention to have said device operate in an orientation-independent manner.

It is further object of the invention to incorporate within said device additional physiological sensors, such that the device will enable a comprehensive physical check-up to be performed by the user inserting the device into his/her mouth and holding it using the defined finger positions.

The present invention has both a device and a system aspect. The device aspect is an oral ECG device shaped like and used like a digital thermometer, which also incorporates a temperature sensor within its tip. Said device further comprises two contact electrodes located on the body of the device, configured for contact with the left and right hands. The mechanical arrangement is such that the device is held in two hands and inserted into the mouth such that the tip is placed under the subject's tongue. By so doing, the temperature and ECG of the subject are measured simultaneously. The device may further comprise additional sensors including but not limited to a pulse-oximetry sensor configured for contact with one of the hands, and microphone(s) for listening to respiratory sounds within the oral cavity. Advantageously, the use of multiple sensors simultaneously in this manner enables a broad, multi-parameter medical check-up to be performed within the simple and familiar framework of "taking your temperature".

Figure 2A:
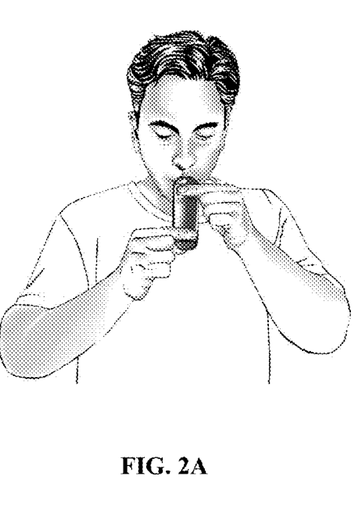
FIGS. 2a, and 2b show the device of the present invention held in two different orientations.
Figure 2B:
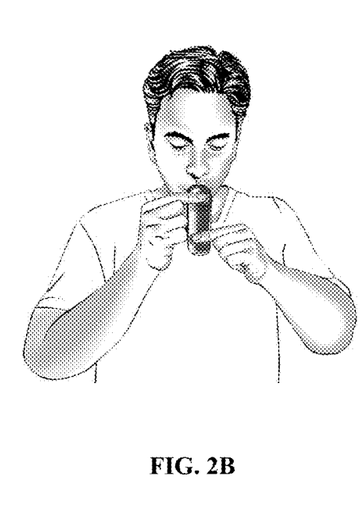

The ECG measured by said device is the classic Lead-I ECG trace from LA to RA. In FIG. 2a below, the left hand/arm (LA) is applied to the proximal electrode (the one nearest the mouth) and the right-hand (RA) is applied to the distal electrode, whereas FIG. 2b illustrates the configuration where these two arms are reversed. As either of these configurations is possible, it is unknown in advance which hand the subject will apply to which of the electrodes. In order to solve this problem while not constraining the user, an algorithm (described below) determines whether the ECG trace needs to be inverted and, if so, performs this inversion automatically. Advantageously, this ensures that the operation of said device is orientation-independent and thus the classic Lead-I ECG trace is always produced.

The system aspect of the current invention involves the transmission of said ECG measurement to a remote device such as a smartphone or computer, where the ECG trace and/or Average Complex can be displayed. As the ECG trace is the classic Lead-I trace, it follows that the Average Complex derived from it is also standard, and is thus suitable for calculating therefrom the calculated cardiac parameters PR Interval, ST Segment, QT Interval, QRS Width, etc. Furthermore, the trends of said calculated cardiac parameters can be graphed or otherwise followed, in order to track physiological changes in the heart. This standard information—ECG traces, Average Complexes and calculated cardiac parameters—can all be stored in a server for remote tracking and/or for access by remotely-located medical personnel.

DETAILED DESCRIPTION OF THE INVENTION

Figure 1B:
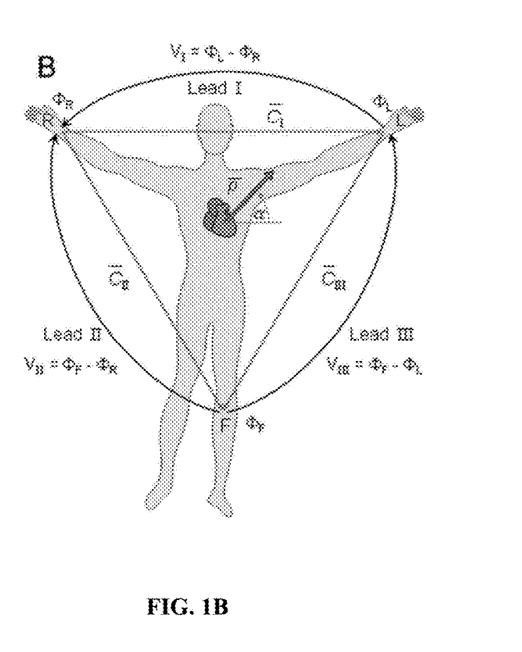

FIGS. 1*a* and 1*b* show the Waller scheme for an ECG versus the classic scheme for an ECG, respectively.

Figure 3A:
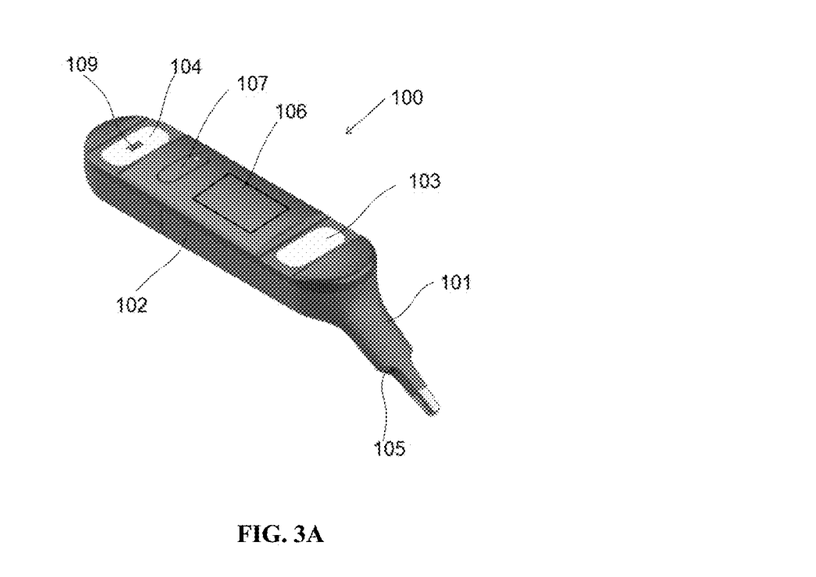
FIGS. 3a and 3b provide upper and lower perspective views of a preferred embodiment of the device.
Figure 3B:
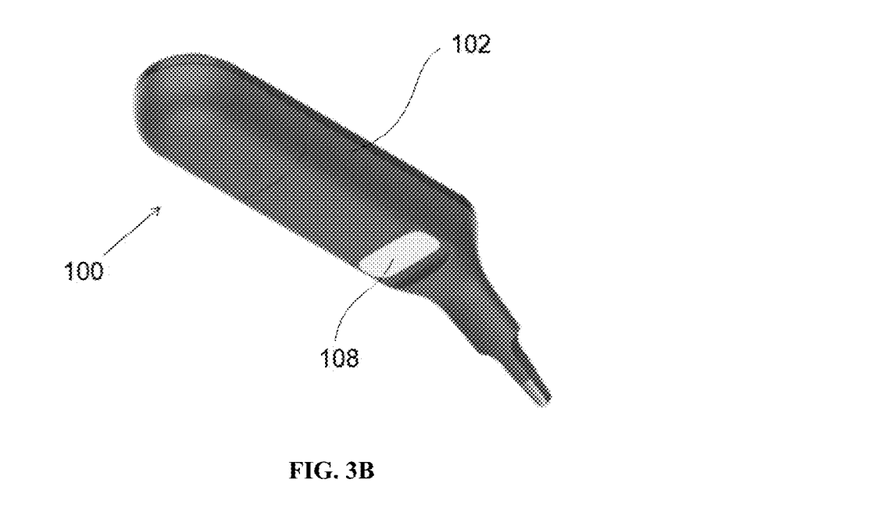

Referring now to FIG. 3*a*, a preferred embodiment of the device 100 of the present invention is shown. Said device comprises a mouthpiece 101 and a body 102, where said body comprises a proximal electrode 103 close to the mouthpiece 101, a distal electrode 104 toward the other end of the device, microphone access hole(s) 105, an integral display 106 and a button 107. Referring now to FIG. 3*b*, the underside of said preferred embodiment is illustrated, showing a potential location for a third or reference electrode. Depending on the specific electronic arrangement of the ECG circuit, sometimes the electronic arrangement is such that a reference electrode 108 is also needed as part of the circuit to measure the Lead-I signal. In the embodiment shown, this reference electrode 108 is located such that when the subject's finger is located on the proximal electrode 103, his/her corresponding thumb is placed on the reference electrode 108.

As used herein, the term "orientation-independent" means that the device may equally well be used with the left-hand placed on the proximal electrode (while the right-hand is placed on the distal electrode) as shown in FIG. 2*a*, or with the right-hand placed on the proximal electrode (while the left-hand is placed on the distal electrode) as shown in FIG. 2*b*.

In the preferred embodiment shown, note that the mouthpiece 101 is tilted downwards with respect to the body 102. Advantageously, this obviates the need for the user to cause the hand which is in contact with the distal electrode 104 to be held above mouth level—which would be uncomfortable.

A potential advantage of simultaneously monitoring ECG and temperature is that a fever is known to cause electrocardiographic changes that can mimic life-threatening conditions [Mody, P., Pandey, A. & Joglar, J. "*Fever Induced Electrocardiographic Changes*", J. Gen Intern Med 30, 136-137 (2015)]. An elevated body temperature measured by the device 100 can therefore serve as an indication that the ECG trace generated by the device 100 is less reliable.

The embodiment shown in FIG. 3*a* shows a pulse oximetry sensor 109 disposed proximate to distal electrode 104, such that the patient's hand is in contact with both the contact electrode 104 and the pulse oximetry sensor 109. For example, the pulse oximetry sensor 109 may be disposed within a contact electrode 104, as shown, or adjacent to it. This provides additional functionality to the device 100 while also enabling ECG-pulse oximeter sensor fusion, for example to provide cross-verification between the heart rate as measured by the ECG and the pulse rate measured by the pulse oximetry sensor 109.

In a preferred embodiment of said device, said device 100 further comprises a communication means such that the ECG and other parameters measured by the device 100 may be communicated to a remote smartphone and/or server and/or computer. For example, this communication means may be a Bluetooth or WiFi communication circuit or chip, to provide short-range communication to a nearby smartphone or WiFi hub; for processing and display of the data there and/or relaying of the data to a remote server. Alternatively, the communication means employed by the device may directly implement long-range communication, for example via a SIM card for a 3/4/5G cellular connection or via a 5G modem for direct 5G data communication.

Figure 4:
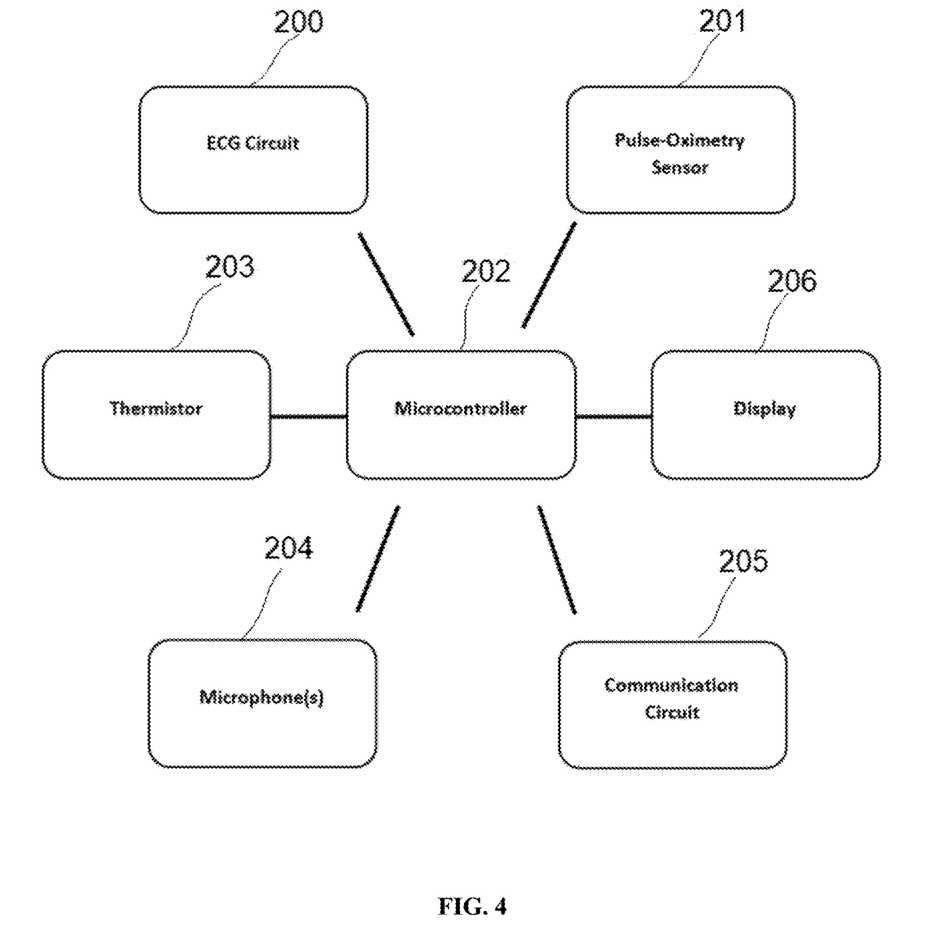
FIG. 4 shows a block diagram of a preferred embodiment on the device.

Referring now to FIG. 4, a block diagram of the electronics of said preferred embodiment is shown. An ECG circuit 201 for a 1-lead device 100 may comprise a MAX86150 bio-sensor module from Maxim Integrated (San Jose, USA). Advantageously, this module contains both an ECG circuit 200 and a pulse-oximetry circuit 201. For embodiments comprising a thermometer, a thermistor 203 for temperature sensing may comprise an MF51E2252F3950C thermistor from Cantherm (Montreal, Canada). A microprocessor or microcontroller for device 202 may comprise one of the PSoC 63 family MCU from Cypress Semiconductors (San Jose, California, USA). Some embodiments comprise one or more microphones 204, for recording the respiratory sounds detected within the oral cavity. Suitable potential microphones for this purpose include digital microphones like the MP34DT06J PDM-type microphone from STMicroelectronics NV (Eindhoven, Holland); and sensitive analog microphones such as the CMC-4015-25L100 electret condenser microphone from CUI Devices (Lake Oswego, OR, USA). Some embodiments comprise a communication circuit 205, for wireless or wired communication with an external device. However, in a further preferred embodiment, the microcontroller 202 comprises built-in communication functionality, such as Bluetooth Low Energy (BLE), such that a separate communication chip is not required. The display 206 can employ any kind of small display screen technology, including by not limited to LCDs and OLEDs. Said display can either be permanently viewed on the body of the device (as shown), or may be "hidden" under a semitransparent surface, such that numbers and/or icons displayed on the LCD/OLED only become visible at the time of their presentation on the display.

The electronic circuit of said device 100 will typically be implemented using a printed circuit board mounted within the device 100 and also include a battery (both not shown).

In a preferred embodiment, the ECG circuit 200 samples the 1-Lead ECG signal via the electrodes 103 and 104, and stores this sampling data in its internal memory. Preferably a signal of 20 seconds or more is sampled and stored in this fashion. On conclusion of the reading, this data buffer is transmitted to an external device for display and analysis.

Figure 5:
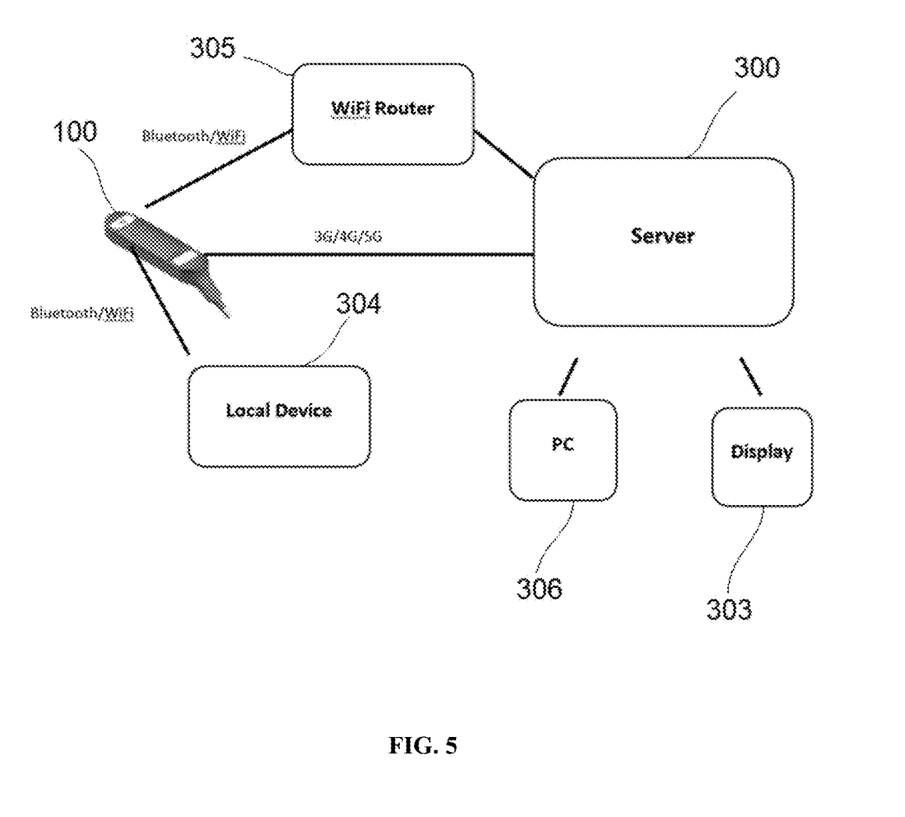
FIG. 5 provides a schematic view of the system aspects of the present invention.

While, obviously, the ECG trace could be displayed on the display 206 of the device, in the preferred embodiment described herein, this ECG data is transmitted onwards for display and analysis on smartphones and/or computers having a larger display. Referring now to FIG. 5, a system diagram of the preferred configurations for displaying and analyzing the ECG signal is provided. As shown in FIG. 5, the device 100 can transmit the ECG signal in one of the following manners: (a) directly to a remote server 300 via 3G/4G/5G communications, (b) to a WiFi router 305 which forwards the data via the Internet to the remote server, or (c) via Bluetooth/WiFi to a local device 304 such as a smartphone, tablet, PC or WiFi router. In the last of these cases, the local smart device (smartphone/tablet/PC) can be used to display the ECG trace and potentially also the Average Complex derived from it. From the server 300, the display of cardiac data can be shown either on a locally-connected display 303 or via a PC 306 connected to the server 300 via the Internet, for example on the PC's browser or dedicated app.

Prior to any display of the ECG trace (and/or Average Complex), it must first be determined whether the data is oriented correctly, and thus the following algorithm is applied:
1) Detect all the P-QRS-T complexes.
2) Calculate the median of the sections of approximately 300 ms in length of the filtered ECG trace which directly precede and follow each given P-QRS-T complex. Then set that median as zero for the complex, such that the complex is adjusted up or down as required.
3) Then sum the data points of each P-QRS-T complex after said adjustment.
4) If this summation yields a positive number, then a positive counter is increased. Otherwise, a negative counter is increased.
5) After all the complexes are evaluated in this way, if the positive counter is bigger than the negative counter, then the data may be presented "as is" on the trace. The reason for this is that Lead-I is a positive lead in the LA-RA orientation, and thus the positive counter will typically be bigger than the negative counter when the device is being used in this orientation.
6) If the negative counter is bigger than the positive counter (i.e., the device is being held in the opposite orientation), then the trace needs to be inverted.

Applying this algorithm ensures that—whether the device is held in the orientation shown in FIG. 2a or that shown in FIG. 2b—the ECG is always displayed in its correct orientation. In this manner, as opposed to what would occur in the Waller scheme (where reversal of the hands would result in entirely different ECG results), the use of the classic Lead-I in combination with the above automatic inversion algorithm advantageously ensures consistent results irrespective of the hand orientation used.

This automatic inversion algorithm may be applied either in the local device 304 or in the server 300 prior to display on a connected screen—whether a "dumb" display 302 or a connected PC 301. Note also that the local device may perform the ECG presentation in this way, and also transmit the ECG data onwards to the server 301 for further display and/or analysis.

Figure 6:
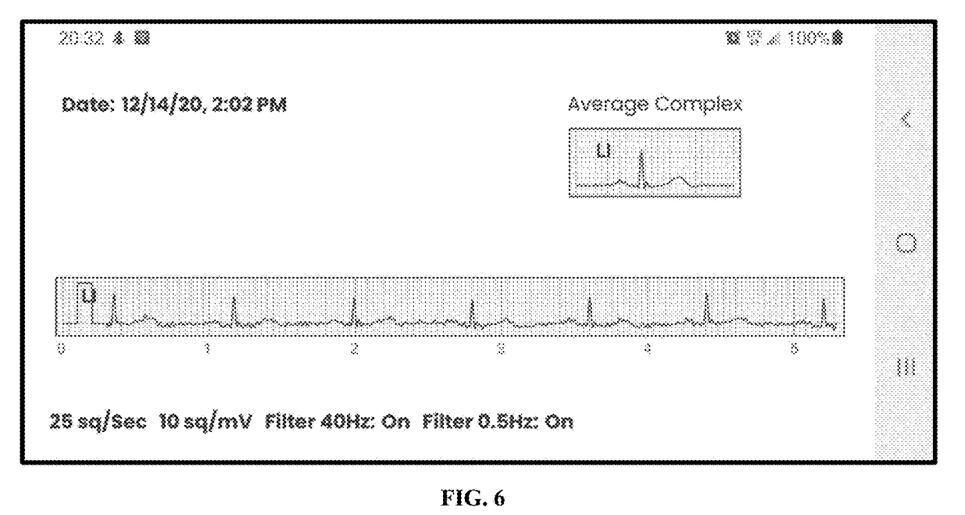
FIG. 6 provides an example of the type of display that can be provided on a smartphone as part of the system aspect of the present invention.
Figure 7:
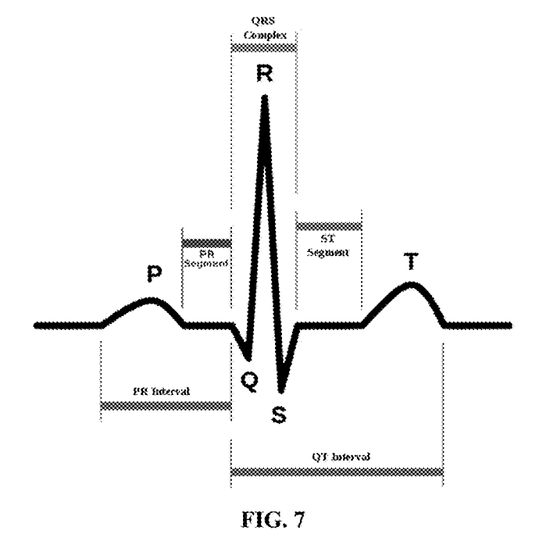
FIG. 7 serves to describe the structure of an Average Complex.

Referring now to FIG. 6, a typical display of the ECG trace as presented on a smartphone is shown. It is important that the ECG trace displayed be a standard one, as two levels of data processing are applied to it. First, the Average Complex is calculated from the trace as a whole, potentially after filtering out any parts of the trace that are corrupted by noise. To illustrate this, FIG. 7 shows the structure of the Average Complex. The QRS complexes in the trace (after filtering) are averaged in order to create the Average Complex. The amplitudes of the different waves (in mV) and the distances between the waves (in mS) can then be calculated as shown in this figure; yielding these calculated cardiac parameters PR Interval, ST Segment, QT Interval, QRS Width, etc.

The trends of these calculated cardiac parameters reveal important information about changes in the physiology of the heart. For example, the PR interval is the time from the beginning of the P wave (atrial depolarization) to the beginning of the QRS complex (ventricular depolarization). The normal PR interval measures 0.12-0.20 seconds (120-200 milliseconds). A prolonged or shortened PR interval can indicate certain diseases. When prolonged, a first degree AV block is present. When shortened, Wolff-Parkinson-White syndrome or Lown-Ganong-Levine syndrome should be suspected.

Figure 8:
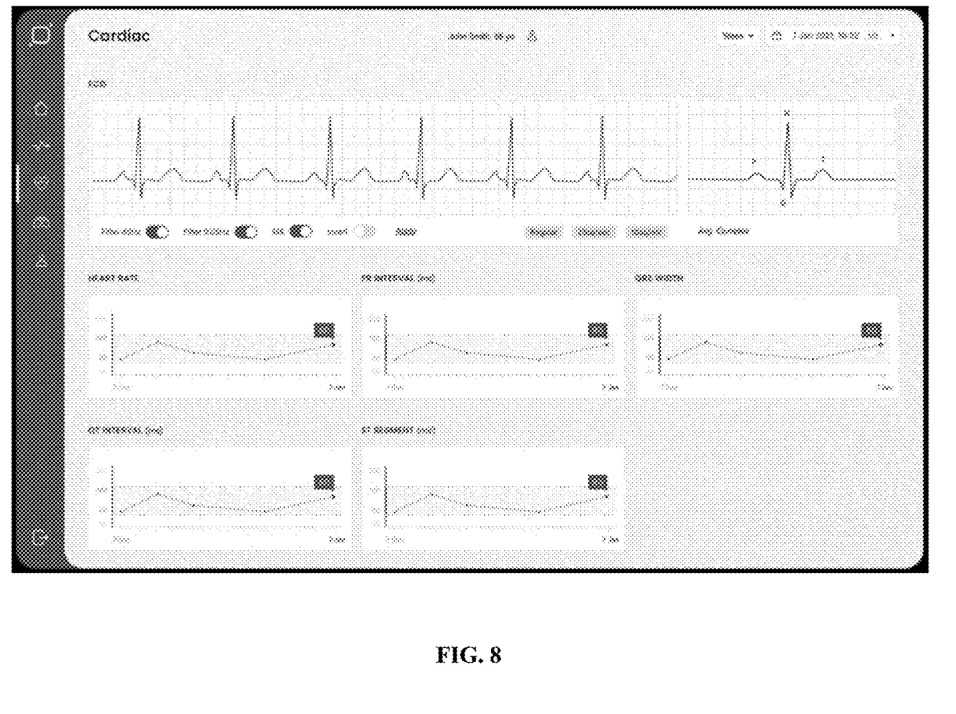
FIG. 8 provides an example of the type of display that can be provided to a remote physician as part of the system aspect of the present invention.

Accordingly, when there are persistent changes in these cardiac parameters over time, there is importance to showing this in graphic form so that the trend can be easily viewed. FIG. 8 provides a preferred embodiment (portal) for displaying the trends of the cardiac parameters together with the ECG on a PC 301 or other display device 302 receiving data from the server. Given that the data for the graphs displayed therein derives from a classic Lead-I ECG trace—measured in an orientation-independent manner—a remote physician is assured that, even though the patient is remote, the information shown in the portal is what he/she would expect to see during an in-person cardiology visit.

The invention claimed is:
1. A system for viewing the Lead-I ECG trace comprising:
at least one oral ECG device for recording ECG signals and temperature of an individual; said oral ECG device comprising:
 a mouthpiece further comprising a temperature sensor; said mouthpiece insertable into said individual's mouth; and
 a body further comprising a proximal electrode and a distal electrode for recording Lead-I of an ECG, said proximal and distal electrodes are holdable by left and right hands of said individual in either orientation; each hand being in an electric contact with one of said proximal and distal electrodes;
 a microcontroller preprogrammed for processing electric signals from said temperature sensor, proximal electrode and distal electrode;
 said proximal and distal electrodes are holdable by left and right hands and said temperature sensor is positionable within said individual's mouth in a concomitant manner; and
 a local device or remote server in wired or wireless communication with said device configured for processing and displaying said Lead-I ECG trace,
wherein said local device or remote server is further configured to provide said Lead-I ECG trace in an orientation-independent manner by summing data points therealong, said Lead-I ECG trace comprising a plurality of P-QRS-T complexes; determining an orientation of said Lead-I ECG trace by, for each P-QRS-T complex in said plurality of P-QRS-T complexes, determining a sum of data point values for said P-QRS-T complex, counting a number of positive sums of data point and counting a number of negative sums of data point values; if a number of negative sums of data point values be greater than a number of positive sums of data point values, inverting said orientation of said Lead-I ECG.

2. The system of claim 1, wherein said local device or remote server is further configured to calculate from said received signals an Average Complex, or to calculate from said received signals an Average Complex and to derive cardiac parameters from said Average Complex.

3. The system of claim 2, further configured for at least one of presenting on said local device or remote server said Average Complex or presenting on said local device or remote server said cardiac parameters derived from said Average Complex.

4. The system of claim 1, wherein said device comprises a sensor selected from the group consisting of a pulse-oximetry sensor, and a microphone arranged for in-mouth operation and combination thereof.

5. The system of claim 1, wherein said device comprises communication means selected from the group consisting of a BLUETOOTH® connection, a WiFi® connection, a 3G connection, a 4G connection, a 5G connection or any combination thereof.

6. A method for viewing a Lead-I ECG trace comprising:
providing at least one oral ECG device for recording an ECG signal and temperature of an individual; said oral ECG device comprising:
a mouthpiece further comprising a temperature sensor; said mouthpiece insertable into said individual's mouth; and
a body further comprising a proximal electrode and a distal electrode for recording Lead-I of an ECG, where said proximal and distal electrodes are holdable by left and right hands of said individual in either orientation; each hand being in an electric contact with one of said proximal and distal electrodes;
a microcontroller preprogrammed for processing electric signals from said temperature sensor, proximal electrode and distal electrode;
said proximal and distal electrodes are holdable by left and right hands and said temperature sensor is positionable within said individual's mouth in a concomitant manner; and
a local device or remote server in wire or wireless communication with said device configured for processing and displaying said Lead-I ECG trace;
holding said proximal and distal electrodes of said at least one oral ECG device by said left and right hands in a separate manner and inserting said temperature sensor of said at least one oral ECG device into said mouth in concomitant manner; and
measuring electric signals from said temperature sensor, proximal electrode and distal electrode;
transmitting measured electric signals to said local device or remote server;
processing said measured electric signals such that said Lead-I ECG trace is obtained; and
displaying said Lead-I ECG trace;
wherein said processing comprises providing said Lead-I ECG trace in an orientation-independent manner by summing data points therealong, said Lead-I ECG trace comprising a plurality of P-QRS-T complexes; determining an orientation of said Lead-I ECG trace by, for each P-QRS-T complex in said plurality of P-QRS-T complexes, determining a sum of data point values for said P-QRS-T complex, counting a number of positive sums of data point and counting a number of negative sums of data point values; if a number of negative sums of data point values be greater than a number of positive sums of data point values, inverting said orientation of said Lead-I ECG.

7. The method according to claim 6, additionally comprising a step of said local device or remote server calculating from said received signals an Average Complex, or calculating an Average Complex and deriving cardiac parameters from said Average Complex.

8. The method according to claim 7, additionally comprising a step selected from the group consisting of presenting on said local device or remote server said Average Complex, presenting on said local device or remote server said cardiac parameters derived from said Average Complex, or any combination thereof.

9. The method according to claim 6, additionally comprising steps of providing a sensor selected from the group consisting of a pulse-oximetry sensor, a microphone arranged for in-mouth operation and combination thereof and measuring electric signals therefrom.

10. The method according to claim 6, wherein said step of intercommunicating said at least one oral ECG device and said local device or remote server by means of communication means selected from selected from the group consisting of a BLUETOOTH® connection, a WiFi® connection, a 3G connection, a 4G connection, a 5G connection or any combination thereof.

* * * * *